United States Patent
Sorrentino

(10) Patent No.: US 7,962,988 B2
(45) Date of Patent: Jun. 21, 2011

(54) TOOTHBRUSH WITH POWERED HEAD

(75) Inventor: Alan Sorrentino, Cranbury, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 12/827,953

(22) Filed: Jun. 30, 2010

(65) Prior Publication Data

US 2010/0263143 A1    Oct. 21, 2010

Related U.S. Application Data

(63) Continuation of application No. 11/624,763, filed on Jan. 19, 2007, now Pat. No. 7,761,946.

(51) Int. Cl.
*A61C 17/22* (2006.01)
(52) U.S. Cl. .......................................... 15/22.1; 15/22.2
(58) Field of Classification Search .................. 15/22.1, 15/22.2
See application file for complete search history.

(56) References Cited

U.S. PATENT DOCUMENTS

| | | | |
|---|---|---|---|
| 5,259,083 A | 11/1993 | Stansbury | |
| 5,416,942 A | 5/1995 | Baldacci et al. | |
| 5,524,312 A | 6/1996 | Tan et al. | |
| 5,617,603 A | 4/1997 | Mei | |
| 6,000,083 A | 12/1999 | Blaustein | |
| 6,347,425 B1 | 2/2002 | Fattori et al. | |
| 6,779,851 B2 | 8/2004 | Bouchiere | |
| 6,952,854 B2 | 10/2005 | Blaustein et al. | |
| 6,966,093 B2 | 11/2005 | Eliav et al. | |
| 7,007,332 B2 | 3/2006 | Hohlbein | |
| 2003/0140436 A1 | 7/2003 | Gatzemeyer et al. | |
| 2003/0226223 A1 | 12/2003 | Chan | |
| 2004/0010869 A1 | 1/2004 | Fattori et al. | |
| 2004/0060137 A1 | 4/2004 | Eliav | |
| 2004/0083566 A1 | 5/2004 | Blaustein | |
| 2006/0000038 A1 | 1/2006 | Gatzemeyer et al. | |
| 2006/0000039 A1 | 1/2006 | Fattori et al. | |
| 2006/0117505 A1 | 6/2006 | Chan | |

FOREIGN PATENT DOCUMENTS

| | | |
|---|---|---|
| DE | 102005009065 | 12/2006 |
| JP | 10-66704 | 3/1998 |
| WO | WO 02/082947 | 10/2002 |
| WO | WO 2006/055574 | 5/2006 |

*Primary Examiner* — Mark Spisich
(74) *Attorney, Agent, or Firm* — Amy M. Fernandez

(57) ABSTRACT

A powered toothbrush includes a handle having a neck. A head is mounted to the neck and has a first surface and an opposed second surface. At least one fixed tuft block is mounted to the head in a fixed orientation and has a plurality of tooth cleaning elements extending outwardly away from the first surface. A movable tuft block is flexibly connected to each fixed tuft block and has a plurality of tooth cleaning elements extending outwardly away from the first surface. A drive assembly is operably connected to the movable tuft block to move the movable tuft block with respect to each fixed tuft block.

7 Claims, 4 Drawing Sheets

TOOTHBRUSH WITH POWERED HEAD

CROSS-REFERENCE TO RELATED PATENT APPLICATIONS

The present application is a continuation of U.S. patent application Ser. No. 11/624,763, filed Jan. 19, 2007 now U.S. Pat. No. 7,761,946, the entirety of which is hereby incorporated by reference.

FIELD OF THE INVENTION

This invention relates generally to toothbrushes, and, in particular, to a toothbrush with a powered head having fixed and movable tuft blocks.

BACKGROUND OF THE INVENTION

A variety of toothbrush configurations exist that have stationary and/or mechanically-driven movable cleaning elements. These conventional toothbrushes are dedicated to tooth cleaning/polishing operations and typically include a head portion directed to the cleaning/polishing operations, and a handle portion. The head typically has a flat or slightly altered surface to which tooth cleaning elements are attached, or to which mechanically-driven movable carriers for the tooth cleaning elements are attached.

Conventional toothbrushes have tooth cleaning elements that extend from a rigid head. Teeth and gums by nature have a complex intricate contour. Due to the rigid nature of the attachment of the tooth cleaning elements to the head of the toothbrush, the orientation of the tooth cleaning elements is not flexible and thus conventional toothbrushes do not provide optimal cleaning of teeth and gums. Conventional toothbrushes therefore have great difficulty in contacting areas of the teeth located at a greater distance from the head, including interproximal spaces between teeth.

It would be desirable to provide a powered toothbrush that reduces or overcomes some or all of the difficulties inherent in prior known devices. Particular objects and advantages will be apparent to those skilled in the art, that is, those who are knowledgeable or experienced in this field of technology, in view of the following disclosure of the invention and detailed description of certain embodiments.

SUMMARY OF THE INVENTION

The principles of the invention may be used to provide a powered toothbrush with at least one fixed tuft block and at least one movable tuft block driven by a drive assembly. In accordance with a first aspect, a powered toothbrush includes a handle having a neck. A head is mounted to the neck and has a first surface and an opposed second surface. At least one fixed tuft block is mounted to the head in a fixed orientation and has a plurality of tooth cleaning elements extending outwardly away from the first surface. A movable tuft block is flexibly connected to each fixed tuft block and has a plurality of tooth cleaning elements extending outwardly away from the first surface. A drive assembly is operably connected to the movable tuft block to move the movable tuft block with respect to each fixed tuft block In accordance with another aspect, a powered toothbrush includes a handle having a neck. A head is mounted to the neck and has a first surface and an opposed second surface. A first fixed tuft block is mounted to the head in a fixed orientation. A second fixed tuft block is mounted to the head in a fixed orientation and is spaced from the first tuft block. A movable tuft block is flexibly connected to the first fixed tuft block and the second fixed tuft block by an elastomeric member. A drive assembly is operably connected to the movable tuft block to move the movable tuft block in an oscillating manner with respect to the first and second fixed tuft blocks.

In accordance with a further aspect, a powered toothbrush includes a handle having a neck. A head is mounted to the neck and has a first surface and an opposed second surface. A first fixed tuft block is mounted to a distal end of the head in a fixed orientation. A second fixed tuft block is mounted to a proximate end of the head in a fixed orientation and spaced from the first tuft block. A movable tuft block is flexibly connected to the first tuft block and the second tuft block by an elastomeric membrane and has a base portion including a slot. A battery is mounted inside the handle, and a motor is operably connected to the battery. A drive shaft is rotatably driven by the motor and has an offset portion that engages the slot in the movable tuft block to drive the movable tuft block in an oscillating manner.

Substantial advantage is achieved by providing a powered toothbrush with at least one fixed tuft block and at least one movable tuft block driven by a drive assembly. In particular, certain embodiments improve cleaning of teeth and gums, and provide improved access to and contact with areas of the teeth located at a distance from the head, including interproximal spaces between the teeth.

These and additional features and advantages disclosed here will be further understood from the following detailed disclosure of certain embodiments.

Figure 1:
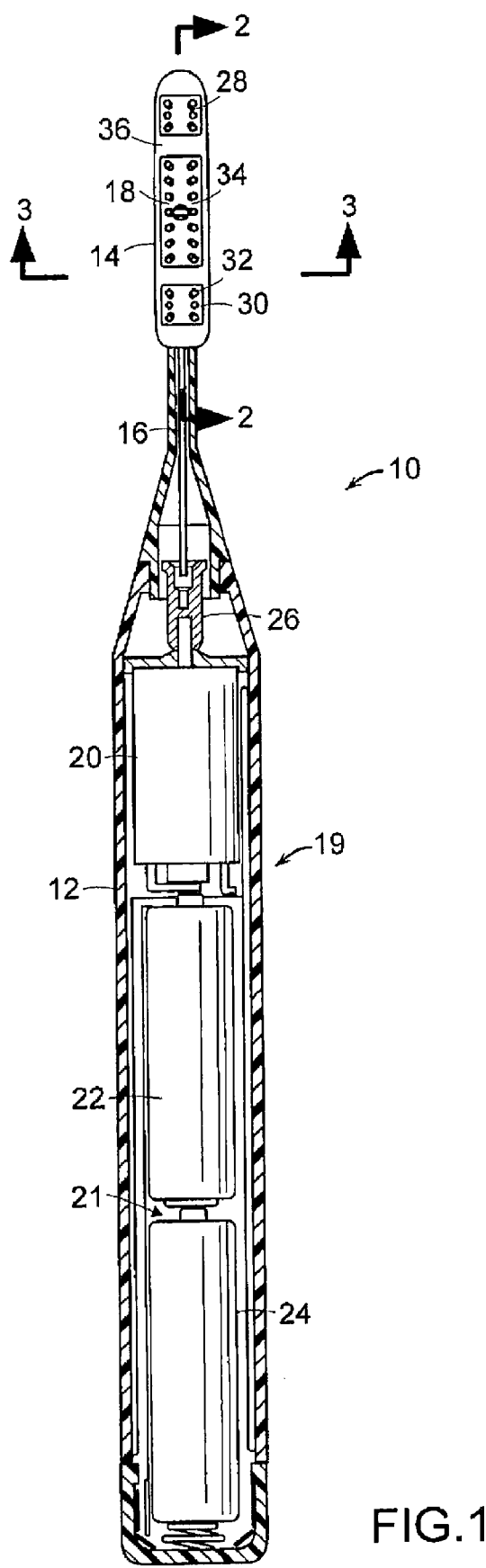
FIG. 1 is a partial sectional bottom view of a toothbrush.

The figures referred to above are not drawn necessarily to scale and should be understood to provide a representation of the invention, illustrative of the principles involved. Some features of the toothbrush with a powered head depicted in the drawings have been enlarged or distorted relative to others to facilitate explanation and understanding. The same reference numbers are used in the drawings for similar or identical components and features shown in various alternative embodiments. Toothbrushes with a powered head as disclosed herein would have configurations and components determined, in part, by the intended application and environment in which they are used.

DETAILED DESCRIPTION OF THE DRAWINGS

Referring to the drawings, in FIG. 1 a toothbrush 10 includes a handle 12 at a first end of the toothbrush, a head 14 at a second end of the toothbrush, and a rotatable shaft 16 extending from handle 12 to head 14. Handle 12 provides compartments for holding a drive assembly 19 including an electric motor 20 and a power source 21. In certain embodiments, power source 21 is formed of two batteries 22, and 24. A shaft coupling 26 is arranged to grip one end of shaft 16 and allow the shaft to be pulled out for cleaning or replacement.

Head 14 may be replaceable, or it may be permanently attached to handle 12. Head 14 includes a plurality of tooth cleaning elements on a first surface 18 thereof. As use herein, the term "tooth cleaning elements" includes any type of structure that is commonly used or is suitable for use in providing oral health benefits (e.g., tooth cleaning, tooth polishing, tooth whitening, massaging, stimulating, etc.) by making intimate contact with portions of the teeth and gums. Such tooth cleaning elements include but are not limited to tufts of bristles that can be formed to have a number of different shapes and sizes, massage elements, and elastomeric cleaning members that can be formed to have a number of different shapes and sizes, or a combination of both tufts of bristles and elastomeric cleaning members. The tooth cleaning elements may be arranged on head 14 in any configuration.

In embodiments in which head 14 includes bristle tufts, the tufts may be formed with bristles of the same or different bristle materials (such as nylon bristles, spiral bristles, rubber bristles, etc.). Moreover, while the tooth cleaning elements of head 14 may be arranged so that they are generally perpendicular to first surface 18 of head 14, some or all of the tooth cleaning elements may be angled at various angles with respect to the first surface 18. When first surface 18 includes bristle tufts, it is thereby possible to select the combination of bristles configurations, bristle materials and bristle orientations to achieve specific intended results and operational characteristics, thus maximizing and enhancing cleaning, tooth polishing, tooth whitening, massaging, and stimulation.

The tooth cleaning elements may be arranged by any conventional method. For example, the tooth cleaning elements may be stapled to head 14. In certain embodiments, the tooth cleaning elements in the form of strands or bristles can be attached via in-molded technology (IMT) methods that generally require small cross-sections of material into which the strands are permanently attached. The strands utilizing IMT methods may be attached during formation of the handle 12 or during formation of head 14, which is the portion of toothbrush 10 to which the strands and other materials are attached.

In other embodiments, tooth cleaning elements in the form of strands or bristles may be attached via anchor free tufting (AFT). In the AFT brush making process, described in detail in U.S. Pat. No. 6,779,851, nylon is fed into a pre-molded plate that can be made from any thermoplastic or elastomer material or combination thereof. This nylon may be processed into bristle tufts of various sizes and shapes. The non-use or proximal end of the nylon is heated and melted to retain the nylon in the brush head when a reasonable pulling force is applied. This head plate may then be ultrasonically welded to a pre-molded handle that has a peripheral wall or frame on which the head plate will rest and become fused to the handle.

Head 14 includes a first fixed tuft block 28 at a distal end thereof, and a second fixed tuft block 30 spaced from first fixed tuft block 28 at a proximal end of head 14. Each of first fixed tuft block 28 and second fixed tuft block 30 have a plurality of tooth cleaning elements 32 projecting outwardly from first surface 18 thereof. As noted above, tooth cleaning elements 32 can be any type of tooth cleaning elements such as bristles, massage elements, and elastomeric fingers or walls.

A movable tuft block 34 having a plurality of tooth cleaning elements 32 is positioned between first fixed tuft block 28 and second fixed tuft block 30. Movable tuft block 34 is flexibly connected to first fixed tuft block 28 and second fixed tuft block 30, allowing relative movement of third tuft block 34 with respect to first and second fixed tuft blocks 28, 30. This movement, in turn, allows tooth cleaning elements 32 of movable tuft block 34 to contact other areas of the teeth located at a greater distance from the head, including interproximal spaces between teeth.

Figure 2:
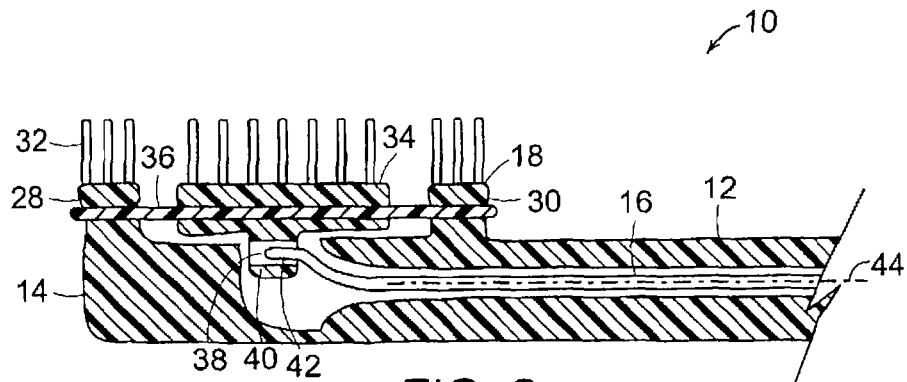
FIG. 2 is a sectional view of the head of the toothbrush of FIG. 1, taken along section line 2-2.

In certain embodiments, movable tuft block 34 is flexibly connected to first fixed tuft block 28 and second fixed tuft block 30 by a flexible member. The flexible member may be formed of any flexible or moldable material including thermoplastic elastomer (TPE), thermoplastic urethane (TPU), rubber, or silicone, for example. The flexible member may be a flexible membrane 36, as seen in FIGS. 1-2. Flexible membrane 36 may be formed of an elastomeric material such as a soft thermoplastic elastomer (TPE), or a blend of polypropylene (PP) and soft TPE, for example. Other suitable materials for flexible membrane 36 will become readily apparent to those skilled in the art, given the benefit of this disclosure. The width and/or thickness of flexible membrane 36 can be adjusted to vary the amount of force needed to move movable tuft block 34 such that its tooth cleaning elements 32 are positioned to achieve their greatest cleaning potential.

Figure 3:
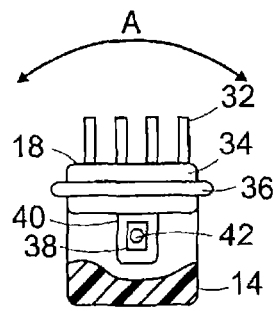
FIG. 3 is a sectional view of the head of the toothbrush of FIG. 1, taken along section line 3-3.

Movable tuft block 34 has a slot 38 formed therein as seen in FIGS. 2-3. In the illustrated embodiment, slot 38 is formed in tuft block base portion 40 that extends from movable tuft block 34 toward an interior of head 14. Shaft 16 has a remote-most end 42 that is off-set from a central longitudinal axis 44 of shaft 16. Remote-most end 42 extends into slot 38 of movable tuft block 34. When shaft 16 is rotated by motor 20, remote-most end 42 describes a circle about shaft 16 and drivingly engages slot 38 to cause movable tuft block 34 to move with respect to first fixed tuft block 28 and second fixed tuft block 30. The width of slot 38 may be generally the same as the diameter of remote-most end 42, as seen in FIG. 3, to leave minimum play; thus keeping noise to a minimum during use. Shaft 16 is preferably of unitary, that is, one-piece construction, and is formed of a single length of a thin rod and shaped as shown. However, it is possible to arrange for remote-most end 42 to be separately formed or provided and fixed to a straight end part of shaft 16.

As shown in the embodiment illustrated in FIGS. 2-3, movable tuft block 34 is driven in a rocking manner laterally with respect to longitudinal axis 44 of shaft 16. That is, movable tuft block 34 rotates in oscillating fashion in the direction of arrow A in a plane extending substantially perpendicular to longitudinal axis 44 and first surface 18 of head 14.

Figure 4:
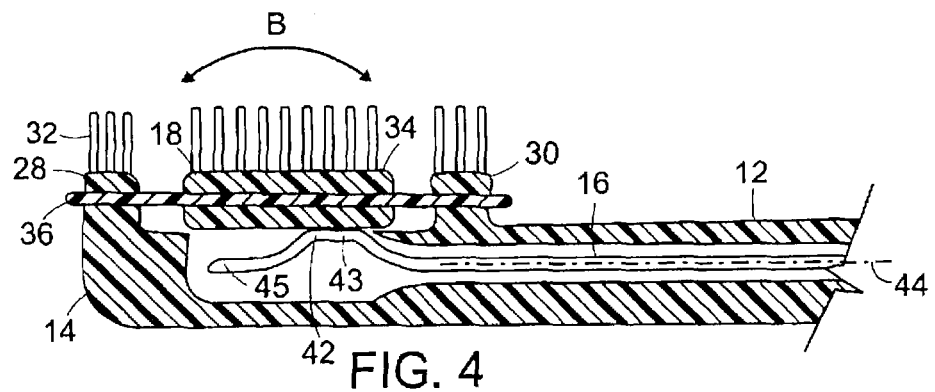
FIG. 4 is a sectional view of an alternative embodiment of the head of the toothbrush of FIG. 1, taken along section line 2-2.

It is to be appreciated that movable tuft block 34 can be driven by drive assembly 19 in many different directions and in different ways. For example, as seen in FIG. 4, remote-most end 42 may have a first offset portion 43 and a second offset portion 45 positioned 180° from first offset portion 43 about longitudinal axis 44. Remote-most end 42 is configured such that first offset portion 43 and second offset portion 45 are positioned so as to alternately engage the proximate and distal ends, respectively, of movable tuft block 34 as shaft 16 rotates. This alternate engagement of the proximate and distal ends of movable tuft block 34 causes movable tuft block 34 to rotate in oscillating fashion in the direction of arrow B in a plane extending along longitudinal axis 44 of shaft 16 and substantially perpendicular to first surface 18 of head 14. It is to be appreciated that in certain embodiments, remote-most end 42 could be configured with a single offset portion such that it strikes only one of the proximate and distal ends of movable tuft block 34 to produce oscillating movement of movable tuft block 34.

Figure 5:
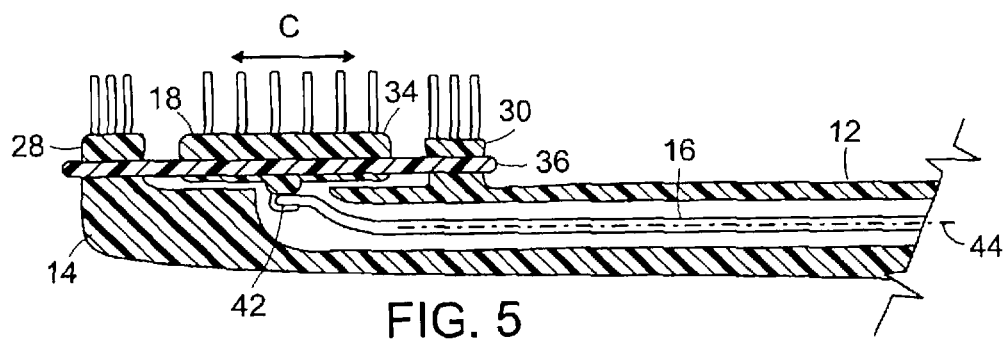
FIG. 5 is a sectional view of another alternative embodiment of the head of the toothbrush of FIG. 1, taken along section line 2-2.

In another embodiment, as illustrated in FIG. 5, shaft 16 is directly connected to movable tuft block 34 by way of base portion 40. Shaft 16 is configured to move in reciprocating fashion along longitudinal axis 44, thereby causing movable tuft block 34 to move along arrow C in a plane extending along longitudinal axis 44 of shaft 16 and substantially parallel to first surface 18 of head 14.

In certain embodiments, shaft 16 can be replaced with another drive member. For example, as seen in FIG. 5, rather than shaft 16, a cable 16 is secured to base portion 40. Thus, as cable 16 is pulled toward handle 12, movable tuft block 34 moves with respect to first tuft block 28 and second tuft block 30. To cause an oscillating movement of movable tuft block 34 in such an embodiment, the cable would be pulled and released in intermittent fashion at a desired frequency. In such an embodiment, the resiliency of flexible membrane 36 allows movable tuft block 34 to return to its natural steady state condition each time the tension is released from the cable.

Thus, it can be seen that movable tuft block 34 can be caused to be moved with respect to first fixed tuft block 28 and second fixed tuft block 30 in many different directions, and in many different ways. The resiliency of flexible membrane 36 allows this relative movement between movable tuft block 34 and first and second fixed tuft blocks 28, 30. Other suitable mechanisms and methods of moving movable tuft block 34 will become readily apparent to those skilled in the art, given the benefit of this disclosure.

Figure 6:
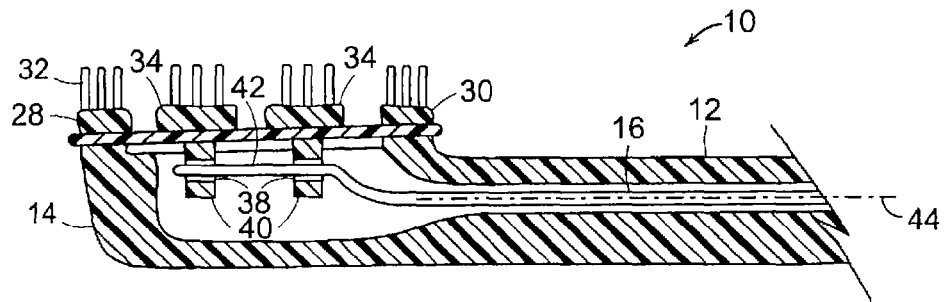
FIG. 6 is a sectional view of a further alternative embodiment of the head of the toothbrush of FIG. 1, taken along section line 2-2.

In certain embodiments, more than one movable tuft block 34 can be provided on head 14. For example, as seen in FIG. 6, two movable tuft blocks 34 are flexibly connected to first fixed tuft block 28 and second fixed tuft block 30 by flexible membrane 36. It is to be appreciated that any number of movable tuft blocks 34 can be flexibly connected to first fixed tuft block 28 and second fixed tuft block 30. Similarly, it is to be appreciated that any number of fixed tuft blocks can be positioned on head 14. Thus, only one, or more than two, fixed tuft blocks on head 14 would also be considered to be within the scope of the present invention.

Figure 7:
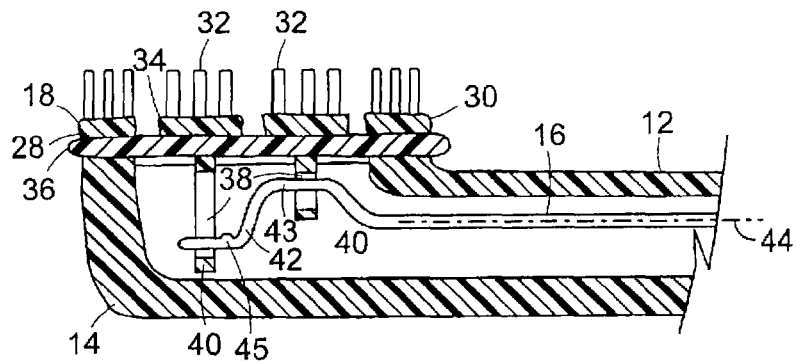
FIG. 7 is a sectional view of a further alternative embodiment of the head of the toothbrush of FIG. 1, taken along section line 2-2.

In certain embodiments where two movable tuft blocks 34 are provided, as seen in FIG. 7, remote-most end 42 may have a first offset portion 43 and a second offset portion 45 positioned 180° from first offset portion 43 about longitudinal axis 44. Remote-most end 42 is configured such that first offset portion 43 extends through the slot 38 formed in the proximal movable tuft block 34 and second offset portion 45 extends through the slot 38 formed in the distal movable tuft block 34. Thus, as shaft 16 rotates, the proximal and distal movable tuft blocks 34 are caused to oscillate in opposite directions in a plane extending substantially perpendicular to both longitudinal axis 44 of shaft 16 and first surface 18.

Figure 8:
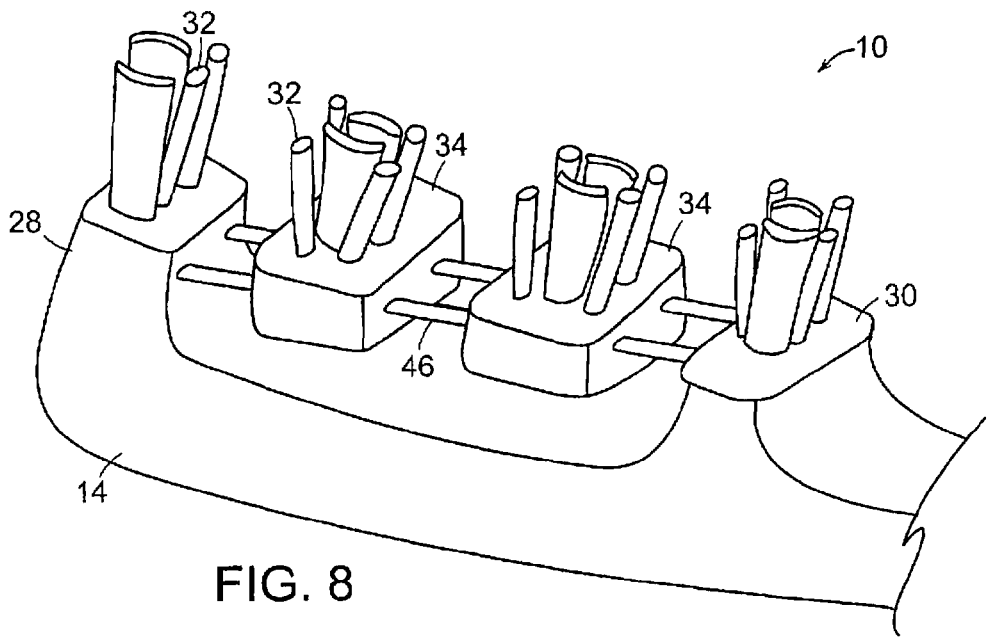
FIG. 8 is a perspective view of yet another alternative embodiment of the head of the toothbrush of FIG. 1.

It is to be appreciated that in other embodiments, movable tuft block 34 may be flexibly connected to first and second fixed tuft blocks 28, 30 by a flexible member having a different configuration than flexible membrane 36. For example, as seen in FIG. 8, movable tuft block 34 is flexibly connected to first fixed tuft block 28 and second fixed tuft block 30 by a plurality of flexible bridge members 46 with voids or gaps provided between the separate bridge members. The flexible bridge members 46 may be formed of any suitable flexible material, such as the materials described above with respect to flexible membrane 36, for example. The width and/or thickness of bridge members 46 can be adjusted to vary the amount of force needed to move movable tuft block 34 such that its tooth cleaning elements 32 are positioned to achieve their greatest cleaning potential.

Figure 9:
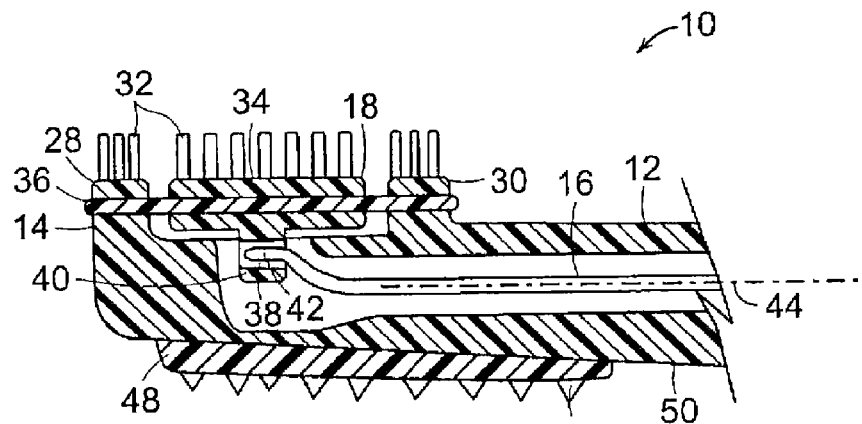
FIG. 9 is a sectional view of another alternative embodiment of the head of the toothbrush of FIG. 1, taken along section line 2-2.

In certain embodiments, as shown in FIG. 9, head 14 may include a tissue cleanser 48 on a second surface 50 of head 14 opposite that of first surface 18. Tissue cleanser 48 may be formed of an elastomeric material, such as a biocompatible resilient material suitable for uses in an oral hygiene apparatus. To provide improved comfort as well as cleaning benefits, the elastomeric material preferably has a hardness property in the range of A8 to A25 Shore hardness. As an example, one embodiment of an elastomeric material is styrene-ethylene/butylene-styrene block copolymer (SEBS) manufactured by GLS Corporation. It is to be appreciated that SEBS material from other manufacturers, or other materials within and outside the noted hardness range could be used. Suitable materials for tissue cleanser 48 will become readily apparent to those skilled in the art, given the benefit of this disclosure.

Tissue cleanser 48 may be configured with a plurality of tissue engaging elements 52, which may be formed as nubs. As used herein a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height.

Nubs 52 are designed to significantly reduce a major source of bad breath in people and improve hygiene. Nubs 52 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, nubs 52 provide for gentle engagement with the soft tissue while reaching downward into the recesses of adjacent papillae of the tongue. The elastomeric construction of nubs 52 also enables them to follow the natural contours of the oral tissue surfaces, such as the tongue, cheeks, lips, and gums of a user. Moreover, the soft nubs 52 are able to flex as needed to traverse and clean the soft tissue surfaces in the mouth along which they are moved.

Figure 10:
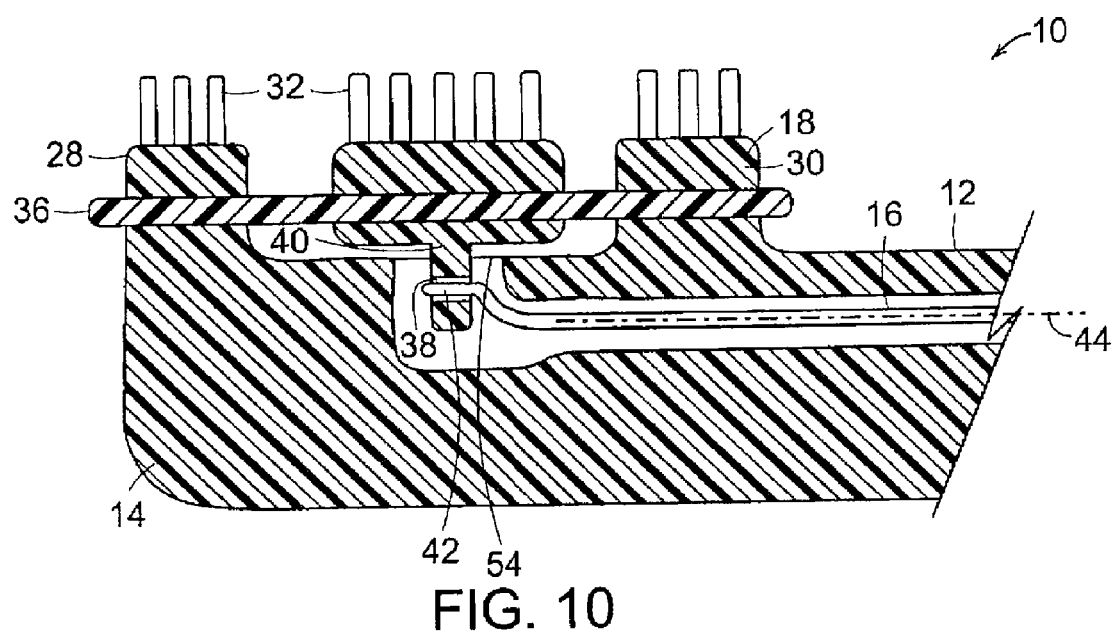
FIG. 10 is a sectional view of another further alternative embodiment of the head of the toothbrush of FIG. 1, taken along section line 2-2.

In certain embodiments, as shown in FIG. 10, a sealing member 54 may be provided about base portion 40, extending between head 14 and extension member 40 of movable tuft block 34. Sealing member 54 serves to reduce the chances of infiltration into drive assembly 19. Sealing member 54 may be formed of a resilient material, such as rubber or any other suitable flexible material.

In light of the foregoing disclosure of the invention and description of various embodiments, those skilled in this area of technology will readily understand that various modifications and adaptations can be made without departing from the scope and spirit of the invention. All such modifications and adaptations are intended to be covered by the following claims.

What is claimed is:

1. A powered toothbrush comprising:
   a handle having a neck;
   a head mounted to the neck and having a first surface and an opposed second surface;
   a first fixed tuft block mounted to the head in a fixed orientation and having a plurality of tooth cleaning elements extending outwardly away from the first surface;
   a second fixed tuft block mounted to the head in a fixed orientation and having a plurality of tooth cleaning elements extending outwardly away from the first surface;
   a movable tuft block flexibly connected to the first and second fixed tuft blocks and having a plurality of tooth cleaning elements extending outwardly away from the first surface;
   a drive assembly operably connected to the movable tuft block to move the movable tuft block with respect to the first and second fixed tuft blocks;
   wherein the first and second fixed tuft blocks and the movable tuft block are aligned along a longitudinal axis of the head; and
   wherein the drive assembly rocks the movable tuft block in an oscillating manner-in a plane extending along the longitudinal axis and substantially perpendicular to the first surface.

2. The powered toothbrush of claim 1, wherein the movable tuft block is secured to the first and second tuft blocks by a flexible member.

3. The powered toothbrush of claim 2, wherein the flexible member is an elastomeric membrane.

4. The powered toothbrush of claim 1, wherein the drive assembly comprises a power source, and a motor having a shaft with a first offset portion.

5. The powered toothbrush of claim 4, wherein the shaft further comprises a second offset portion that is positioned 180° from the first offset portion.

6. The powered toothbrush of claim 1, wherein the first fixed tuft block is positioned at a distal end of the head and the second fixed tuft block is positioned at a proximate end of the head, the movable tuft block being positioned between the first fixed tuft block and the second fixed tuft block.

7. The powered toothbrush of claim 5, wherein the first offset portion and the second offset portion alternately engage the movable tuft block as the shaft rotates thereby rocking the movable tuft block.

* * * * *